(12) United States Patent
Dacus et al.

(10) Patent No.: US 12,150,859 B2
(45) Date of Patent: Nov. 26, 2024

(54) DUAL MOBILITY ACETABULAR COMPONENT

(71) Applicant: Joint Development, LLC, Salt Lake City, UT (US)

(72) Inventors: Eric M. Dacus, Salt Lake City, UT (US); Thomas Collier, Park City, UT (US)

(73) Assignee: Joint Development, Inc., Salt Lake City, UT (US)

( * ) Notice: Subject to any disclaimer, the term of this patent is extended or adjusted under 35 U.S.C. 154(b) by 117 days.

(21) Appl. No.: 17/381,135

(22) Filed: Jul. 20, 2021

(65) Prior Publication Data
US 2022/0015912 A1     Jan. 20, 2022

Related U.S. Application Data

(60) Provisional application No. 63/054,173, filed on Jul. 20, 2020.

(51) Int. Cl.
*A61F 2/34*     (2006.01)
*A61F 2/30*     (2006.01)

(52) U.S. Cl.
CPC .............. *A61F 2/34* (2013.01); *A61F 2/3094* (2013.01); *A61F 2002/30451* (2013.01);
(Continued)

(58) Field of Classification Search
CPC ...................... A61F 2/34; A61F 2/3094; A61F 2002/30451; A61F 2310/00023; A61F 2310/00077; A61F 2310/00083; A61F 2310/00592; A61F 2002/3208; A61F 2/32; A61F 2002/345; A61F 2002/3448
See application file for complete search history.

(56) References Cited

U.S. PATENT DOCUMENTS 4,535,486 A * 8/1985 Roberts .................. A61L 27/34
                                                          623/22.21
5,725,589 A * 3/1998 Pfaff ........................ A61F 2/34
                                                          623/22.29
(Continued)

FOREIGN PATENT DOCUMENTS

EP            1611869 A1 *  1/2006  ............... A61F 2/32
WO    WO-2007121242 A2 * 10/2007  ............... A61F 2/30

OTHER PUBLICATIONS

Translation of Jani et al. (WO2007121242) retrieved from https://worldwide.espacenet.com/patent/search/family/038610359/publication/WO2007121242A2?q=WO2007121242 retrieved on Oct. 10, 2023 (Year: 2023).*

*Primary Examiner* — Ariana Zimbouski
*Assistant Examiner* — Yasniary De La Caridad Morales
(74) *Attorney, Agent, or Firm* — Lowry Blixseth APC; Scott M. Lowry

(57) ABSTRACT

The dual mobility acetabular component includes an acetabular cup and a liner that engage one another in a relatively static relationship by way of a Morse taper. The acetabular cup and the liner may be manufactured from a metal material (e.g., titanium) that decreases the energy differential therebetween, to limit or eliminate the galvanic cell phenomenon that forms between adjacent surfaces thereof as a result of body fluid therein that remains captured in small gaps or spaces due to capillarity. As such, the dual mobility acetabular component may experience reduced fretting compared to conventional hip joints known in the art.

27 Claims, 3 Drawing Sheets

(52) U.S. Cl.
CPC .............. *A61F 2310/00023* (2013.01); *A61F 2310/00077* (2013.01); *A61F 2310/00083* (2013.01); *A61F 2310/00592* (2013.01)

(56) References Cited

U.S. PATENT DOCUMENTS

| | | | | |
|---|---|---|---|---|
| 6,132,469 | A | * | 10/2000 | Schroeder .............. A61F 2/4637 623/22.24 |
| 7,326,253 | B2 | * | 2/2008 | Synder ...................... A61F 2/34 623/22.4 |
| 2002/0052659 | A1 | * | 5/2002 | Hayes, Jr. .............. A61L 27/306 623/22.24 |
| 2003/0153981 | A1 | * | 8/2003 | Wang ...................... B22F 3/114 623/22.21 |
| 2008/0208350 | A1 | * | 8/2008 | Roger ....................... A61F 2/34 623/22.24 |
| 2010/0234965 | A1 | * | 9/2010 | Dalla Pria ................ A61F 2/34 623/22.28 |
| 2018/0214274 | A1 | * | 8/2018 | Perez ....................... A61F 2/32 |

* cited by examiner

DUAL MOBILITY ACETABULAR COMPONENT

BACKGROUND OF THE INVENTION

The present invention generally relates to a dual mobility acetabular component. More specifically, the present invention relates to a dual mobility acetabular component that includes an acetabular cup and a liner having interfacing surfaces made from materials that reduce galvanic corrosion and fretting.

Total hip arthroplasty ("THA") is a surgical procedure where the hip joint is replaced by a prosthetic implant known, e.g., as a hip prosthesis, and may be performed for purposes of relieving arthritis pain or to help with a hip fracture. More specifically, THA typically involves replacing the acetabulum and the femoral head, such that the patient effectively receives a new artificial ball-and-socket joint. THA is currently one of the most common orthopaedic operations and is one of the more popular and successful surgical procedures in orthopaedics throughout the world. Of course, given the increasing quantity of THAs performed throughout the world on a yearly basis, reducing and/or preventing medical and mechanical complications continue to remain important.

One type of hip prosthesis uses a dual mobility acetabular component (also known as an unconstrained tripolar implant), which was first introduced in France at the end of the 1970s as an alternative to prosthetic hip-joint sockets known at the time. The dual mobility acetabular component was designed to reduce the risk of THA dislocation and has more recently gained wider attention in the United States as an alternative option in the prevention and treatment of instability in both primary and revision THA, and offers the benefit of increased stability without compromising clinical outcomes and implant longevity.

More specifically, the dual mobility acetabular component includes an acetabular cup designed to be implanted into the natural hipbone socket and may include an outer porous coating to promote bony ingrowth therewith. The acetabular cup is typically made from a titanium alloy, and the dual mobility acetabular component is made from a relatively hard metal material such as cobalt chromium (CoCr), Titanium alloys, or the like capable of remaining resilient under relatively large loads (e.g., during walking or running) and that may otherwise have anti-microbial properties. The dual mobility acetabular component also includes a liner that engages the acetabular cup in friction-fit engagement, such as by way of a Morse taper, to ensure the liner remains substantially stationary relative to the acetabular cup after implantation. The liner may include an inner concave surface designed for select reception of a polymer insert having an outer convex surface and an inner concave surface designed to receive a femoral head therein. The prevailing consensus in the prior art is that the liners, polymer inserts, and femoral heads should all be manufactured from materials known in the art to polish well (e.g., metals or metal alloys, including cobalt chromium; plastic polymers such as ultra-high cross-linked polyethylene ("UHXLPE") or ultra-high molecular weight polyethylene ("UHMWPE"); or ceramics such as zirconia toughened alumina) given that the inner concave surface of the liner, the outer convex surface of the polymer insert, the inner concave surface of the polymer insert, and the outer convex surface of the femoral head are all articulatory surfaces and subject to wear over time. Historically, other materials such as titanium, which do not polish well under prevailing processes used to polish other materials such as cobalt chromium, may undesirably reduce the longevity of the hip implant due to relatively higher friction within the articulatory surface. Articulatory surfaces have also been shown to wear prematurely in metal-on-metal applications where the acetabular cup is made from a metal material different than the liner.

The dual mobility cup is typically considered an enhancement over monobloc acetabular cup designs (e.g., including only an acetabular shell and liner) because the dual mobility cup facilitates articulation in two respects, i.e., one between the femoral head and the polymer insert; and a second between the polymer insert and the stationary liner engaged with the acetabular cup. Monobloc acetabular cup designs, on the other hand, facilitate less articulation, i.e., only between the femoral head and the relatively stationary liner. Thus, the dual motion thereby enhances the amount of articular motion in the hip joint. Although, again, the prior art has stressed the importance of manufacturing the articulatory surfaces from materials that polish well, regardless whether for dual mobility or monobloc embodiments, for longevity purposes.

In this respect, a number of studies have been conducted over the years regarding the impact of design parameters, such as taper region diameter, length, conicity, surface finish, and area of interference, for purposes of understanding and enhancing the mechanical and/or operational limits of the dual mobility acetabular component design. Most of these studies have concentrated on structural designs to reduce loosening, unintended disassembly, and/or fracture, but not the chemistry of the materials themselves. This is because micro-motions between the acetabular cup and the liner are known to cause undesired wear due to, e.g., friction and fretting. Pursuant to these studies, there have been some reductions in fretting and fretting-corrosion phenomenon by reducing critical variances in manufacturing tolerances between the acetabular cup and the liner, and by implementing certain procedures during surgery. Although complete elimination of micro-motion between the acetabular cup and the liner is still not possible. To this end, the relatively high rate of failure of some metal-on-metal hip prosthesis has yet to be curtailed.

More recently, it was discovered that, not only do the micro-motions between the acetabular cup and the liner cause fretting and related corrosion, but fretting and fretting-related corrosion may also be the result of a galvanic cell phenomenon that forms along surfaces of the acetabular cup and liner somewhat offset from one another after implantation. The fact that the liner engages the acetabular cup by a Morse taper produces small gaps or spaces therebetween due to the inexact engagement of the interfacing surfaces. Body fluid may travel up into these gaps or spaces between component parts due to surface tension along facing surfaces of the acetabular cup and the liner (i.e., capillarity). Due to this capillarity, the body fluid may remain within these gaps or spaces without an appreciable amount of fluid exchange over time. In metal-on-metal applications, i.e., where the acetabular cup is manufactured from a metal material different than the liner, the body fluid essentially serves as an electrolytic medium that facilitates the exchange of ions that move between the acetabular cup and the liner due to relative energy differentials. This results in the creation of a subatomic galvanic cell along surfaces where the gaps or spaces between the acetabular cup and the acetabular liner are formed from the Morse taper. In time, this causes surface level ionization of the metal materials. Certainly, in cases where the acetabular cup is manufactured from cobalt chromium, cobalt ions may break free from the implant material and undesirably enter the bloodstream as a result of the galvanic cell process. For example, the use of cobalt chromium as the acetabular cup or liner may produce an electric potential on the order of about −500 mV, which is enough of a difference to set up a galvanic cell.

Fretting and corrosion are known problems that can be exacerbated by friction, and thus the prevailing concentration has been on manufacturing-related solutions related to the use of materials that polish well (e.g., cobalt chromium instead of titanium), as opposed to the chemistry of the materials of the acetabular cup and the liner, especially since the liner also includes an articulatory surface that interfaces with an insert or femoral head. Despite these advances, studies have shown that fretting and corrosion between some metal-on-metal hip prosthesis, while low, are still unacceptably high. A byproduct of increased fretting corrosion in THA is decreased flexural rigidity, which can cause further complications, such as fracture. Accordingly, there is a relatively unacceptably high failure rate, even where the acetabular cup is manufactured from cobalt chromium. Thus, there is a need in the art to reduce, and preferably eliminate, fretting and corrosion-related fretting in THA implants.

There exists, therefore, a significant need for a dual mobility acetabular component that includes an acetabular cup and related liner configured for engagement by a Morse taper and manufactured from materials (e.g., titanium) that reduce or eliminate the energy differential therebetween that causes galvanic corrosion after implantation. The present invention fulfills these needs and provides further related advantages.

SUMMARY OF THE INVENTION

In one embodiment, a dual mobility acetabular component as disclosed herein includes an acetabular cup having an internal curved surface at least partially made from a first material. Moreover, the dual mobility acetabular component may also include a liner having an external curved surface at least partially made from a second material, which the liner is engageable with the internal curved surface of the acetabular cup for locking engagement therewith. The internal curved surface of the acetabular cup may be relatively larger than the external curved surface of the liner thereby allowing the liner to seat therein, whereby a capillarity gap forms between the line and the acetabular cup. Since the first material has an affinity for electrons relatively comparable to that of the second material, this inhibits ionization of the first material relative to the second material across the capillarity gap to substantially reduce and/or eliminate the galvanic cell phenomenon therebetween.

The first material and the second material may both be made from a common material or different materials (including, e.g., different chemical compositions). In one embodiment, the first material and/or the second material may be made from a metal material, such as titanium and/or a titanium alloy. In another embodiment, the first material and/or the second material may be made from a titanium alloy with a ceramicized coating such as titanium nitride or silicon nitride. In yet another embodiment, the first material and/or the second material may be made from a non-magnetic material such as brass, copper, zinc, or an aluminum alloy. Moreover, the acetabular cup may be made from a base material different than the first material and/or the liner may be made from a base material different than the second material. In this embodiment, the first material may be a vapor deposited layer substantially covering the internal curved surface formed from the base material of the acetabular cup and the second material may be a vapor deposited layer substantially covering the external curved surface formed from the base material of the liner. Although, regardless of the type of material, the first material and the second material may each have a chemical composition producing a relatively low energy differential across the capillarity gap when positioned proximate one another. This may be accomplished, e.g., by forming the first material and/or the second material from a low ionizing material.

In another aspect of these embodiments, the liner may engage the acetabular cup about a circumferential cold weld and the capillarity gap may include multiple capillarity gaps formed on each side of the circumferential cold weld. The capillarity gap(s) may serve as a buffer between the first material and the second material where fluid medium may reside after implantation. To this end, the liner may engage the acetabular cup by a Morse taper.

In another embodiment, a dual mobility acetabular component as disclosed herein may include an acetabular cup made from a first material and a liner made from a second material and lockable relative to the acetabular cup in a manner forming a capillarity gap in between the first material and the second material. Here, the first material and the second material may be made from titanium and/or a titanium alloy that generally inhibits ionization across the capillarity gap by way of equalizing an energy potential therebetween.

In one embodiment, the first material and the second material may be different or the same material. Moreover, the acetabular cup may be made from a base material different than the first material, wherein the first material is a vapor deposited layer substantially covering an internal curved surface of the acetabular cup. Additionally, the liner may also be made from a base material different than the second material, wherein the second material may be a vapor deposited layer substantially covering an external curved surface of the liner. The liner may effectively engage the acetabular cup about a cold weld having multiple capillarity gaps formed on each side thereof, and the capillarity gap(s) may serve as a buffer between the first material and the second material.

In another embodiment, a dual mobility acetabular component as disclosed herein may include an acetabular cup having a base material different than a vapor deposited internal curved surface layer and a liner having a base material different than a vapor deposited external curved surface layer that engages the vapor deposited internal curved surface layer in a manner forming a capillarity gap therebetween. Here, the liner may engage the acetabular cup about a circumferential cold weld and the capillarity gap may include multiple capillarity gaps formed on each side of the circumferential cold weld. Additionally, the vapor deposited internal curved surface layer may substantially shield the base material of the acetabular cup and the vapor deposited external curved surface layer may substantially shield the base material of the liner to substantially equalize an energy potential between the acetabular cup and the liner thereby reducing ion exchange across the capillarity gap. As such, the vapor deposited internal curved surface layer may have an affinity for elections relatively comparable to that of the vapor deposited external curved surface layer.

In one embodiment, the base material of the acetabular cup and the base material of the liner may have a relatively higher affinity for electrons when compared to the respective vapor deposited internal curved surface layer and the vapor deposited external curved surface layer. As such, the vapor deposited internal curved surface layer and the vapor deposited external curved surface layer may each have a chemical composition producing a relatively low energy differential across the capillarity gap when positioned proximate one another. This may be accomplished, e.g., by forming the base material of the acetabular cup, the base material of the liner, the first material, and/or the second material from titanium or a titanium alloy. Alternatively, the vapor deposited internal curved surface layer and/or the vapor deposited external curved surface layer may be made from a non-magnetic material such as brass, copper, zinc, or an aluminum alloy.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
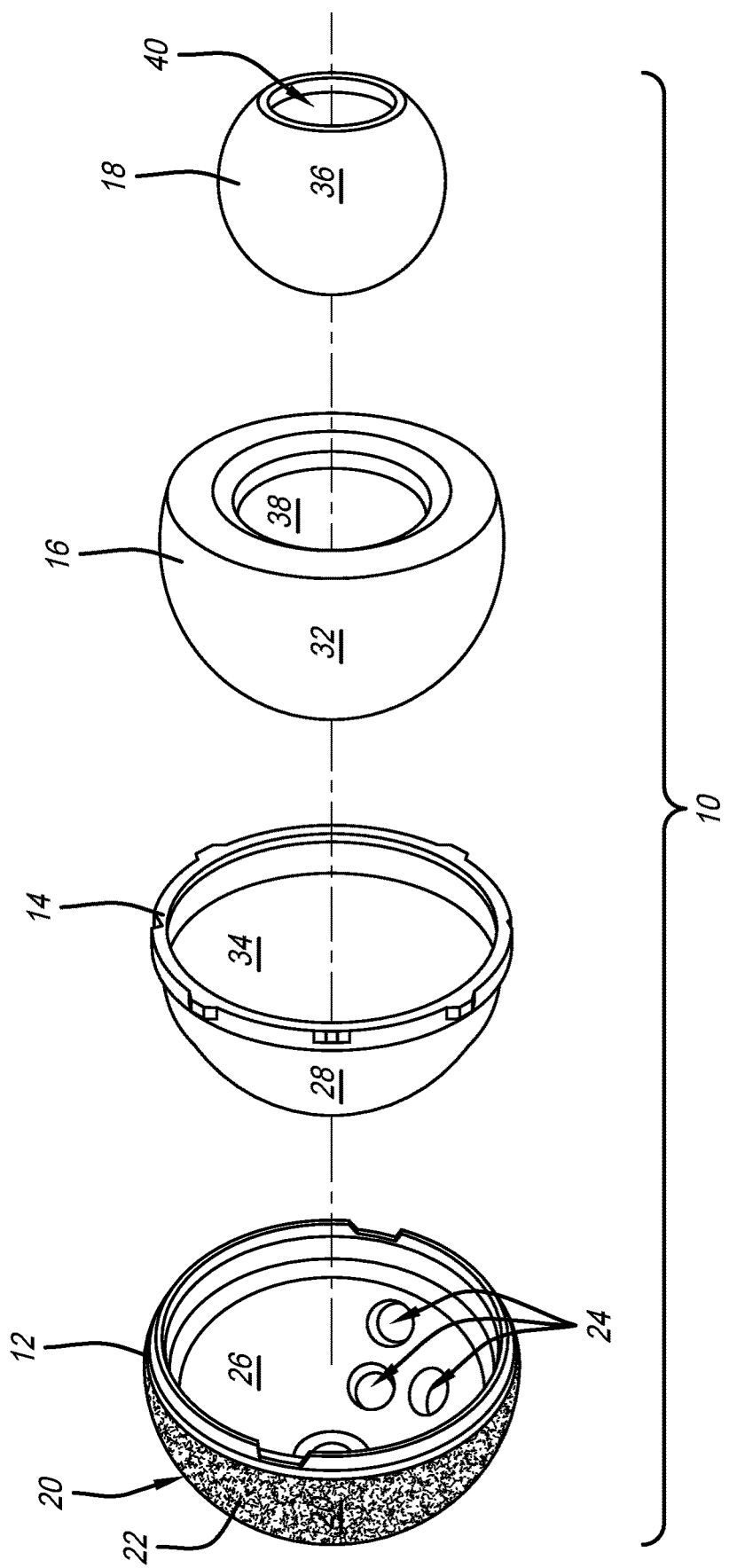
FIG. 1 is an exploded perspective view illustrating a dual mobility acetabular component, including an acetabular cup, a liner, a polymer insert, and a femoral head.

As shown in the exemplary drawings for purposes of illustration, the present invention for a dual mobility acetabular component is generally illustrated in FIGS. 1-5 with respect to reference numeral 10. More specifically, FIG. 1 illustrates the dual mobility acetabular component 10 generally including an acetabular cup or shell 12, a liner 14, and an insert 16. During THA surgery, the acetabular cup 12 is implanted for purposes of providing a "new" socket configured to provide structural support for the other articulatory components of the hip implant, such as the polymer insert 16 and/or a femoral head 18 that couples thereto. In preparation for implantation, a surgeon may resurface or otherwise generally hollow out the bone of the existing hip socket for reception of an outer convex surface 20 of the acetabular cup 12. This outer convex surface 20 may include a porous coating 22 designed to facilitate bony ingrowth after implantation, which may help retain the acetabular cup 12 in place once implanted. Additionally, the acetabular cup 12 may include one or more apertures 24 having a size and shape to selectively receive and retain a comparably sized screw (not shown) having a length that extends through the thickness of the acetabular cup 12 and into engagement with the underlying bone tissue. Of course, these screws may also help provide positive engagement of the porous coating 22 with the hip socket bone, to enhance fixation thereto and to further promote bony ingrowth therewith.

As also illustrated in FIG. 1, the acetabular cup 12 includes a relatively smooth inner concave surface 26 having a size and shape designed to facilitate reception of an outer convex surface 28 of the liner 14. As illustrated in more detail in FIGS. 2-5, the liner 14 couples with the acetabular cup 12 by press-fit engagement by way of a Morse taper between the inner concave surface 26 and the outer convex surface 28. The general principle of the Morse taper is that of a cone in a cone, namely the trunnion (i.e., the outer convex surface 28 of the liner 14) and the bore (i.e., the inner concave surface 26 of the acetabular cup 12) are both relatively uniformly tapered such that when the outer convex surface 28 (bore) of the liner 14 is tapped onto the inner concave surface 26 (trunnion) of the acetabular cup 12, the surface area of the outer convex surface 28 comes into intimate contact with the surface area of the inner concave surface 26. A surgeon may opt to use an impactor during surgery to further engage the Morse taper between the acetabular cup 12 and the liner 14 once the two are appropriately aligned. This should ensure correct seating of the liner 14 within the acetabular cup 12.

In application, the Morse taper results in the conical taper of the inner concave surface 26 compressing the walls in the outer convex surface 28 as it expands therein during impaction. Stresses inside the materials of each of the acetabular cup 12 and the liner 14 keep both components fixed together. The dependent characteristics of the interference fit, such as the pull-out force, insertion force, and stress distribution, depend on the taper angle, contact length, inner and outer diameters of the acetabular cup 12 and the liner 14, depth of insertion, material properties, coefficient of friction, and/or size and/or mass of the additional insert 16 and/or the femoral head 18. The Morse taper is essentially defined by the angle that the tapered surfaces make relative to the longitudinal axis of the dual mobility acetabular component 10 and the relatively small mismatch angle between the outer convex surface 28 and the inner concave surface 26. This relatively small mismatch results in co-integration, or locking engagement, with material transfer across a zone of contact essentially forming "cold welds" therebetween. The degree of interference fit along these "cold welds" is determined by the relative dimensions of the inner concave surface 26 and the outer convex surface 28, and a design decision to have interference along a specific part of the circumference and length of the taper. The area of interference contact must be adequate to maintain integrity under functional loaded conditions, while the surface finish of the components must be specific to the physical and mechanical properties of the materials and capable of retaining the "cold weld" under load, such as during walking or running.

Figure 2:
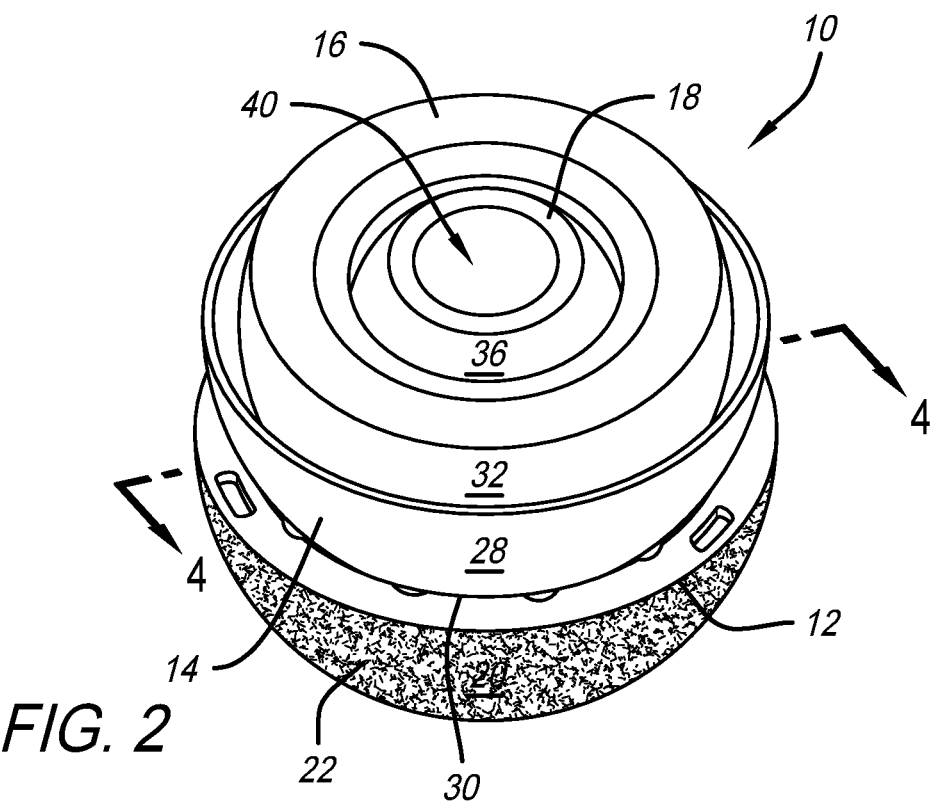
FIG. 2 is a perspective view of the dual mobility acetabular component of FIG. 1 fully assembled, and illustrating the polymer insert in a first position relatively concentric within the liner and the femoral head.
Figure 3:
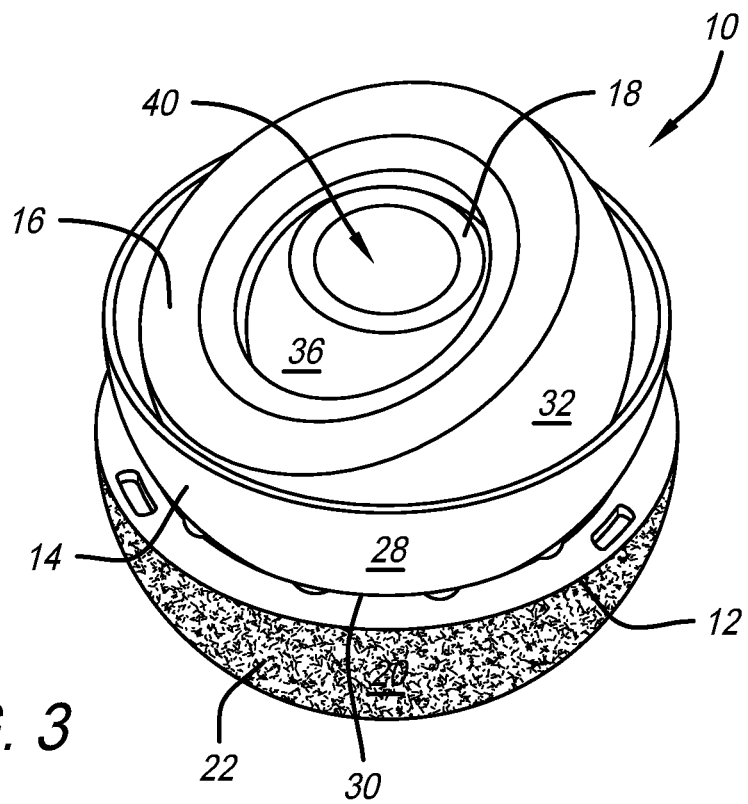
FIG. 3 is a perspective view similar to FIG. 2, illustrating the polymer insert rotated to a second position concentrically offset from the femoral head and the liner.

In this respect, FIGS. 2 and 3 illustrate the dual mobility acetabular component 10 fully assembled. As shown, the liner 14 is in press-fit engagement with the acetabular cup 12 by way of friction fit engagement of the aforementioned Morse taper of the outer convex surface 28 with the inner concave surface 26, and namely about what essentially amounts to a circumferential cold weld 30. While the circumferential cold weld 30 retains the liner 14 in relatively static relation relative to the acetabular cup 12, the polymer insert 16 may generally rotate relative to the liner 14 and/or the acetabular cup 12, as generally illustrated between FIGS. 2 and 3. Such movement is permitted by way of engagement of a relatively smooth outer convex surface 32 of the polymer insert 16 that has a size and shape for select reception and rotational movement within a relatively smooth inner concave surface 34 of the liner 14. Similarly, the femoral head 18 may also move relative to the polymer insert 16, the liner 14, and/or the acetabular cup 12 about a smooth, and relatively smaller, outer convex surface 36 having a size and shape for select reception and rotational movement within a smooth inner concave surface 38 (FIG. 1) of the polymer insert 16. As illustrated in FIGS. 1-4, the femoral head 18 may include a channel 40 for attachment to an extension projecting out from a femoral stem implanted into the base of the femoral bone (not shown). Of course, each of the articular surfaces 32, 34, 36, 38 may be manufactured or otherwise machined to facilitate smooth relative rotational movement akin to that of the natural hip ball-and-socket joint.

To this end, FIG. 2 illustrates the polymer insert 16 in a first position generally concentrically aligned with the femoral head 18, the liner 14, and the acetabular cup 12, while FIG. 3 illustrates the polymer insert 16 in a second position generally offset from concentric alignment with the femoral head 18, the liner 14, and the acetabular cup 12. Obviously, the polymer liner 16 is able to rotate relative to the liner 14 simultaneously while rotating relative to the femoral head 18. The same is true with respect to the femoral head 18, namely the femoral head 18 is able to rotate relative to the polymer insert 16, the liner 14, and/or the acetabular cup 12 to enhance the range of movement of the artificial hip.

Figure 4:
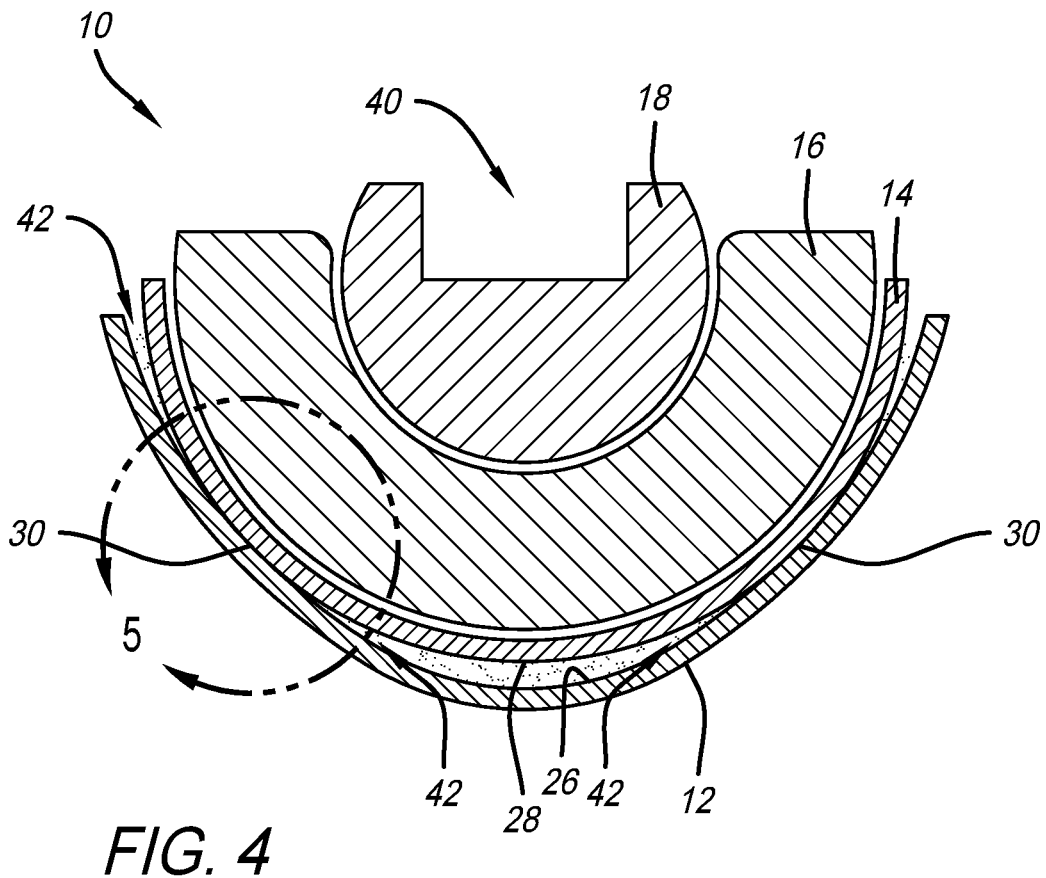
FIG. 4 is a cross-sectional view taken about the line 4-4 in FIG. 2, further illustrating relative positioning of the acetabular cup, the liner, the polymer insert, and the femoral head within the dual mobility acetabular component.
Figure 5:
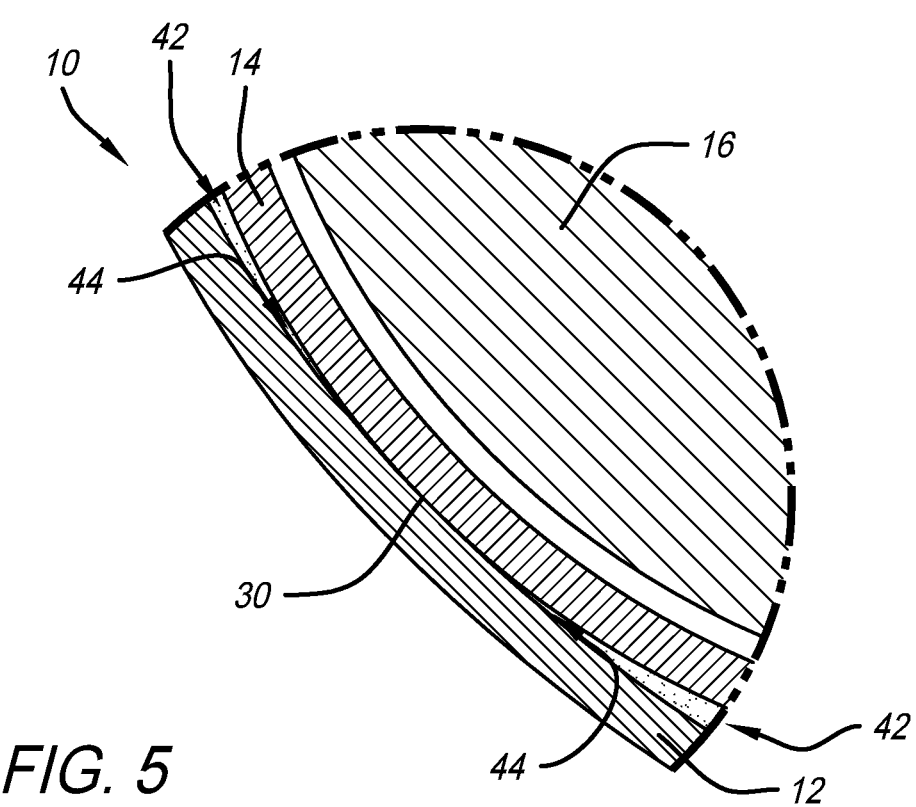
FIG. 5 is an enlarged cross-sectional view taken about the circle 5 in FIG. 4, further illustrating capillary action of a fluid medium between the acetabular cup and the liner.

FIGS. 4 and 5 more specifically illustrate the relative implanted arrangement of the acetabular cup 12, the liner 14, the polymer insert 16, and the femoral head 18. More specifically, FIGS. 4 and 5 illustrate the liner 14 engaged with the acetabular cup 12 about the circumferential cold weld 30. As such, a series of relatively small spaces or gaps 42 (shown in an exaggerated form in FIGS. 4 and 5) are formed on either side of the circumferential cold weld 30 due to the inexact alignment of the surface area of the inner concave surface 26 of the acetabular cup 12 and the surface area of the outer convex surface 28 of the liner 14. These relatively small spaces or gaps 42 permit surrounding body fluid to travel up therein (as indicated by a fluid medium 44 in FIG. 5) and form a buffer between the material forming the outer convex surface 28 of the liner 14 and the material forming the inner concave surface 26 of the acetabular cup 12. This fluid medium 44 may remain substantially stagnant in these gaps or spaces 42 due to capillarity.

Moreover, due to the nature of the structure of the circumferential cold weld 30, the liner 14 may experience micro-motion relative to the acetabular cup 14 along the circumferential cold weld 30 when the hip joint is loaded, such as during walking or running. Of course, such movement causes some level of surface level friction, e.g., due to rubbing of the exterior surface 28 of the liner 14 with the internal surface 26 of the acetabular cup 12.

As briefly discussed above, after implantation, the body fluid making up the fluid medium 44 that travels up into the spaces or gaps 42 between the liner 14 and the acetabular cup 12 may substantially remain therein without any appreciable exchange of new fluid over time as a result of capillarity suction. This fluid may facilitate electrical crossing when there is an energy differential between the liner 14 and the acetabular cup 12, thereby causing surface-level corrosion of the respective surfaces 26, 28 within the joint, which leads to fretting therein as discussed above.

It has been discovered that the related spontaneous redox reactions resultant from the rather unexpected and unintended internal galvanic cell can be significantly mitigated and/or eliminated by equalizing the energy differential between the acetabular cup 12 and the liner 14, despite the continued presence of the fluid medium 44. In this respect, in general, the acetabular cup 12 and the liner 14 of the dual mobility acetabular component 10 disclosed herein may be manufactured or made from materials and/or include surface layer treatments that permit engagement by way of the Morse taper, yet reduce or eliminate the energy differential therebetween, to reduce or eliminate the galvanic cell phenomenon. In one embodiment, this can be accomplished by manufacturing the acetabular cup 12 and the liner 14 from materials that have a comparable affinity for electrons. In a metal-on-metal embodiment, the acetabular cup 12 and the liner 14 may both be manufactured from the same metal material so that the energy differential between the two are roughly equal due to similar chemical composition. In one embodiment in this respect, the acetabular cup 12 and the liner 14 may be manufactured from titanium or a titanium alloy. Titanium and titanium alloys are not readily selected as base materials for joint implants, especially for components that include articulatory surfaces, because titanium and titanium alloys have traditionally had a relatively higher surface roughness and are difficult to polish relative to other materials such as cobalt chromium. Moreover, while titanium and titanium alloys are still known as a relatively weak magnetic (i.e., one that can still induce ion or electron movement), it was unexpected that, when used as the base material for both the acetabular cup 12 and the liner 14, the galvanic cell phenomenon known to cause undesired fretting and fretting-related corrosion was substantially reduced. This appears to be the result of the macro-structure of the titanium subsurface, namely naturally forming a passive film of a few nanometers in thickness, which contains a relatively high concentration of oxygen vacancies. As such, corrosion across the titanium-based surface is controlled by migration of oxygen vacancies. Thus, it was found that titanium on titanium designs performed better than other materials known in the art, such as cobalt chromium, including with an electric potential on the order of about −440 mV. In other words, despite the fact that titanium has a relatively higher surface roughness, the net effect of reducing the unintended internal galvanic cell phenomenon with a metal-on-metal design that includes only titanium was that the hip implant has better resistance to fretting and fretting-corrosion than contemporary designs.

Additionally, a titanium or titanium-based alloy material forming the base material for the acetabular cup 12 and/or the liner 14 may be further modified or treated to include a different surface layer material, e.g., applied thereon by vapor or ion deposition, so long as the energy differential between the acetabular cup 12 and the liner 14 remains substantially balanced.

Alternatively, the acetabular cup 12 and the liner 14 may be made from other metal materials having characteristics designed to limit or reduce galvanic cell phenomenon fretting and/or micro-motion friction during loading. For example, the acetabular cup 12 and the liner 14 may be manufactured from non-magnetic materials such as work hardened brass, copper, zinc, or aluminum alloys, e.g., in combination with or in place of titanium. In other embodiments, the acetabular cup 12 and the liner 14 may be made from different materials, albeit as long as the materials minimize the energy differential therebetween and do not readily ionize. Here, in some embodiments, the acetabular cup 12 and/or the liner 14 may include common or different surface layer treatment (e.g., applied by vapor deposition or ion deposition) having a thickness designed to balance any potential energy differential inherent between two different base metal materials.

In another aspect of these embodiments, the acetabular cup 12 and the liner 14 may include a surface level treatment having a comparable affinity for electrons, regardless of the underlying base material. In this latter embodiment, the acetabular cup 12 may be made from a base material different than the base material of the liner 14 (including, e.g., a base material having a different affinity for electrons, but that may be shielded by the surface level treatment so as to accomplish reducing and/or eliminating the galvanic cell phenomenon as disclosed herein).

In general, the net result of the material selection should be to decrease the energy potential across the fluid medium 44 separating the acetabular cup 12 and the liner 14, to reduce the galvanic cell phenomenon and related fretting and/or fretting-related corrosion in hip implants. Doing so will ultimately reduce ion exchange across the body fluid medium 44 and ultimately reduce surface level corrosion on the outer convex surface 28 of the liner 14 and the interior concave surface 26 of the acetabular cup 12, even if the components are manufactured out of a common material (e.g., titanium) that does not polish as well as other materials known in the art (e.g., cobalt chromium). Consequently, the decreased movement of ions within the spaces or gaps 42 about the fluid medium 44 substantially reduces ionization at the surfaces 26, 28, thereby substantially reducing fretting and fretting-related corrosion. Accordingly, reductions in corrosion-related fretting, even if the hip implant still experiences micro-motion from engagement of the acetabular cup 12 with the liner 14 about the circumferential cold weld 30, will experience less fretting, less corrosion-related fretting, less undesired dispersion of small pieces of metal debris, and better longevity.

Although several embodiments have been described in detail for purposes of illustration, various modifications may be made without departing from the scope and spirit of the invention. Accordingly, the invention is not to be limited, except as by the appended claims.

What is claimed is:

1. A dual mobility acetabular component, comprising:
an acetabular cup having an internal curved surface at least partially comprising a first material; and
a liner having an external curved surface at least partially comprising a second material and engageable with the internal curved surface of the acetabular cup for locking engagement therewith, the internal curved surface of the acetabular cup being larger than the external curved surface of the liner thereby forming a capillarity gap in between when engaged, wherein the first material has an affinity for electrons comparable to that of the second material thereby inhibiting ionization of the first material relative to the second material across the capillarity gap.

2. The dual mobility acetabular component of claim 1, wherein the first material and the second material comprise a titanium material or a titanium alloy material.

3. The dual mobility acetabular component of claim 1, wherein the acetabular cup comprises a base material different than the first material, wherein the first material comprises a vapor deposited layer at least partially covering the internal curved surface.

4. The dual mobility acetabular component of claim 1, wherein the liner comprises a base material different than the second material, wherein the second material comprises a vapor deposited layer at least partially covering the external curved surface.

5. The dual mobility acetabular component of claim 1, wherein the first material and the second material each have a chemical composition eliminating an energy differential across the capillarity gap when positioned proximate one another.

6. The dual mobility acetabular component of claim 1, wherein the first material and the second material comprise a common metal material.

7. The dual mobility acetabular component of claim 6, wherein the common metal material comprises a titanium material or a titanium alloy material.

8. The dual mobility acetabular component of claim 1, wherein the first material and the second material comprise a non-magnetic material selected from the group consisting of brass, copper, zinc, and an aluminum alloy.

9. The dual mobility acetabular component of claim 1, wherein the first material and the second material comprise a an ionization inhibiting material.

10. The dual mobility acetabular component of claim 1, wherein the first material and the second material comprise different chemical compositions.

11. The dual mobility acetabular component of claim 1, wherein the liner engages the acetabular cup about a circumferential cold weld.

12. The dual mobility acetabular component of claim 11, wherein the capillarity gap comprises multiple capillarity gaps formed on each side of the circumferential cold weld.

13. The dual mobility acetabular component of claim 1, wherein the capillarity gap comprises a buffer between the first material and the second material.

14. The dual mobility acetabular component of claim 1, wherein the liner engages the acetabular cup by a Morse taper.

15. A dual mobility acetabular component, comprising:
an acetabular cup comprising a first material; and
a liner comprising a second material and lockable relative to the acetabular cup in a manner forming a capillarity gap in between the first material and the second material, wherein the first material and the second material comprise titanium or a titanium alloy inhibiting ionization across the capillarity gap by way of equalizing an energy potential therebetween.

16. The dual mobility acetabular component of claim 15, wherein the acetabular cup comprises a base material different than the first material, wherein the first material comprises a vapor deposited layer at least partially covering an internal curved surface of the acetabular cup.

17. The dual mobility acetabular component of claim 15, wherein the liner comprises a base material different than the second material, wherein the second material comprises a vapor deposited layer at least partially covering an external curved surface of the liner.

18. The dual mobility acetabular component of claim 15, wherein the first material and the second material comprise a different material.

19. The dual mobility acetabular component of claim 15, wherein the liner engages the acetabular cup about a cold weld having multiple capillarity gaps formed on each side thereof.

20. The dual mobility acetabular component of claim 15, wherein the capillarity gap comprises a buffer between the first material and the second material.

21. A dual mobility acetabular component, comprising:
an acetabular cup having a base material different than a vapor deposited internal curved surface layer; and
a liner having a base material different than a vapor deposited external curved surface layer that engages the vapor deposited internal curved surface layer in a manner forming a capillarity gap therebetween, the vapor deposited internal curved surface layer shielding the base material of the acetabular cup and the vapor deposited external curved surface layer shielding the base material of the liner to equalize an energy potential between the acetabular cup and the liner thereby reducing ion exchange across the capillarity gap.

22. The dual mobility acetabular component of claim 21, wherein the vapor deposited internal curved surface layer has an affinity for electrons comparable to that of the vapor deposited external curved surface layer.

23. The dual mobility acetabular component of claim 21, wherein the base material of the acetabular cup and the base material of the liner comprise titanium or a titanium alloy.

24. The dual mobility acetabular component of claim 21, wherein the base material of the acetabular cup and the base material of the liner have a greater affinity for electrons than the respective vapor deposited internal curved surface layer and the vapor deposited external curved surface layer.

25. The dual mobility acetabular component of claim 21, wherein the vapor deposited internal curved surface layer and the vapor deposited external curved surface layer each have a chemical composition eliminating an energy differential across the capillarity gap when positioned proximate one another.

26. The dual mobility acetabular component of claim 21, wherein the vapor deposited internal curved surface layer and the vapor deposited external curved surface layer comprise a non-magnetic material selected from the group consisting of brass, copper, zinc, and an aluminum alloy.

27. The dual mobility acetabular component of claim 21, wherein the liner engages the acetabular cup about a circumferential cold weld and the capillarity gap comprises multiple capillarity gaps formed on each side of the circumferential cold weld.

* * * * *